(12) United States Patent
Hascoet et al.

(10) Patent No.: US 6,350,232 B1
(45) Date of Patent: Feb. 26, 2002

(54) DEVICE FOR PROTECTING A COVER ON A PROBE

(75) Inventors: Gerard Hascoet; Thierry Pechoux, both of Paris (FR)

(73) Assignee: Arrow International, Inc., Reading, PA (US)

( * ) Notice: Subject to any disclaimer, the term of this patent is extended or adjusted under 35 U.S.C. 154(b) by 0 days.

(21) Appl. No.: 09/522,516

(22) Filed: Mar. 10, 2000

(30) Foreign Application Priority Data

Mar. 17, 1999 (FR) .............................. 99 03293

(51) Int. Cl.⁷ .................................................. A61B 1/04
(52) U.S. Cl. ........................ 600/124; 600/121; 206/364
(58) Field of Search .......................... 206/69, 210, 305, 206/363, 364; 600/121, 123, 124

(56) References Cited

U.S. PATENT DOCUMENTS

| | | |
|---|---|---|
| 3,703,892 A | 12/1970 | Meyers |
| 4,241,828 A | 12/1980 | Bourdelle et al. |
| 4,823,949 A | 4/1989 | Bala |
| 5,259,383 A * | 11/1993 | Holstein et al. ....... 128/660.01 |
| 5,325,846 A | 7/1994 | Szabo |
| 5,406,939 A * | 4/1995 | Bala ............................. 128/4 |
| 5,614,660 A * | 3/1997 | Tanaka ......................... 73/37 |
| 5,765,682 A * | 6/1998 | Bley et al. .................. 206/363 |
| 5,969,223 A * | 10/1999 | Nagai et al. ................ 73/1.06 |

FOREIGN PATENT DOCUMENTS

WO  WO 97/43941  11/1997

* cited by examiner

Primary Examiner—David T. Fidei
(74) Attorney, Agent, or Firm—Amster, Rothstein & Ebenstein

(57) ABSTRACT

The invention relates to a device for protecting a cover. According to the invention, said cover is flexible and tubular in shape being closed at one end and open at its other end, and said cover is disposed at least in part inside a hollow tubular protective element referred to as a protective tube, which element is open at both ends. The device of the invention is particularly suited for use in the medical field, in particular for covering, preferably in sterile manner, a tool that is to be inserted in an animal or a human being, in particular in a natural passage such as the esophagus, the urethra, the rectum, or a blood vessel.

18 Claims, 5 Drawing Sheets

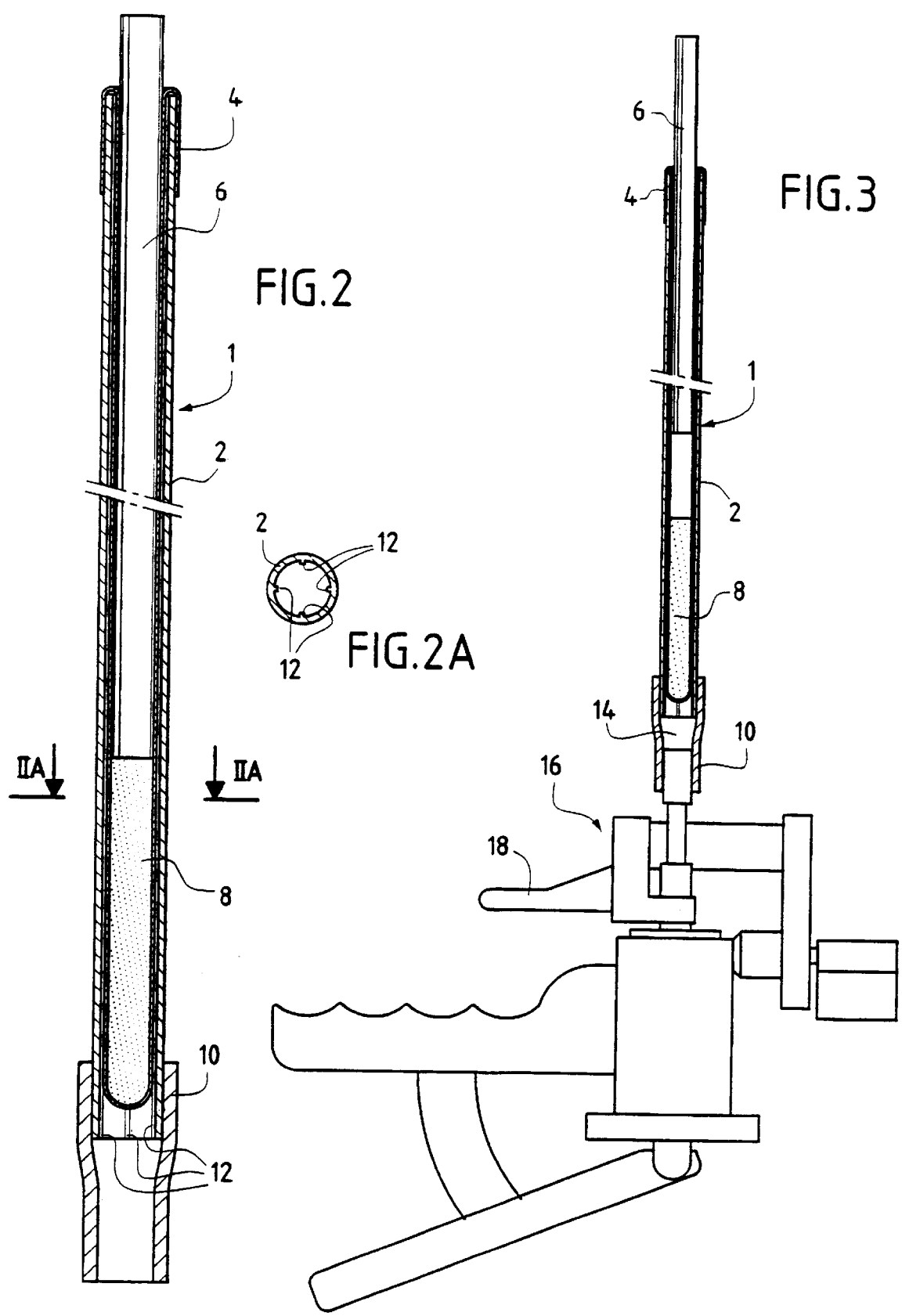

DEVICE FOR PROTECTING A COVER ON A PROBE

The present invention relates to a device for protecting a cover, to the use of a device for protecting a cover, to a method of fitting a cover on a probe, and to a method of making a device for protecting a cover.

BACKGROUND OF THE INVENTION

Patent FR-A-2 695 999=U.S. Pat No. 5,479,928 describes an intracorporeal probe for accurately determining the speed of a liquid medium, and in particular blood flow rate in the aorta. Other intracorporeal probes are known in the medical field for humans and for animals.

Such a probe must be subjected to a sterilization operation prior to be used on a patient. Such sterilization is lengthy, expensive, and difficult to implement. It is necessary to apply sterilization agents which are expensive, and in particular pharmaceuticals, conscientiously to the probe. Care must be taken of the probe while it is being handled in this way since such a probe is fragile and the sterilization agents can be harmful. In addition, it is necessary to renew the sterilization operation on each occasion that the probe is used, thereby increasing the risk of damaging the probe.

It is also possible to use a cover to protect the patient from the transmission of pathogens when such a probe is used. However, such a cover is not easy to fit onto the probe, and in addition care must be taken to ensure that the cover is sterile.

OBJECTS AND SUMMARY OF THE INVENTION

The invention seeks to resolve these problems by proposing a device for protecting a cover that enables the cover to be fitted easily on the probe and that guarantees that the cover is sterile. Thus, the invention guarantees hygiene for the patient during use of the probe without it being necessary to sterilize the probe on each use. The invention thus proposes a solution which is simple, low cost, and easy to implement.

The invention also provides the use of a device for protecting a cover, a method of fitting a cover on a probe, and a method of making a device for protecting a cover.

The device of the invention for protecting a cover can advantageously be employed when using the probe known under the name "DYNEMO 3000", produced by SOMETEC.

More precisely, the invention provides a device for protecting a cover, the device comprising a hollow tubular protective element which is open at both ends, referred to as a protective tube, at least a portion of said cover being placed inside the tube, the cover being flexible and in the form of a tube that is closed at one end and open at its other end.

Such a device makes it possible to use a probe without it being necessary to sterilize said probe. In addition, the cover that is used is easy to fit and to handle.

Preferably, the device has means facilitating insertion of the cover inside the protective tube.

Advantageously, the means for facilitating insertion comprise a flexible coupling mounted on that one of the open ends of the protective tube which is adjacent to the closed end of the cover, specifically so as to enable temporary suction to be established in this region.

Preferably, the protective tube has a plurality of means enabling localized regions to be established in which the cover is not in contact with the inside wall of the protective tube, and in particular internal ridges preferably disposed substantially parallel to the longitudinal axis of the protective tube.

Advantageously, the ridges are continuous, extending substantially from one end to the other of the protective tube, thereby making it possible, for example, to establish temporary suction between the cover and the inside wall of the tube.

Preferably, the cover is flexible and is folded back over the protective tube at its end remote from the closed end of the cover.

Advantageously, the device is made in such a way that the protective tube has an inside wall, and the protective tube has means for holding the cover substantially against the inside wall of the protective tube, e.g. means comprising a rod of appropriate diameter.

Preferably, the cover contains an impedance-matching medium, and in particular a gel, for matching impedance between the cover itself and a measuring element for insertion at least temporarily inside the flexible cover.

Advantageously, said impedance-matching medium is an acoustic impedance-matching medium, thus enabling soundwaves to be transmitted substantially without disturbance.

Preferably, said impedance-matching medium is disposed substantially at the closed end of the cover, said impedance-matching medium, such as a gel, preferably being biocompatible, and better still being edible.

Advantageously, the device is sterilized, in particular packaged in a sterilizable sealed package which is advantageously transparent, at least in part.

Preferably, the cover is of a length that is sufficient to cover the outside surface of an intracorporeal probe, preferably an intracorporeal probe having an ultrasound type measuring element, e.g. for measuring the speed or flow rate of a flowing body fluid, such as blood.

Advantageously, the cover is made of a sterilizable flexible material such as silicone or a natural or synthetic rubber such as SEBS.

The invention also provides the use of a device of the kind described in the medical field in particular for covering, preferably in sterile manner, a tool that is to be inserted in an animal or a human being, in particular in a natural passage such as the esophagus, the urethra, the rectum, or a blood vessel.

The invention also provides a method of fitting a cover on a probe, the cover having one opening and being contained at least in part inside a tube, a device of the kind described being provided, said method comprising the following steps:

the protective tube is coupled to a vacuum pump;

a vacuum is established inside the tube adjacent to the closed end of the cover within a closed space as defined between the cover, the vacuum pump, and the protective element;

the rod is withdrawn while the vacuum is maintained;

the probe is inserted into the cover;

the vacuum is eliminated; and the assembly comprising the probe with the cover mounted thereon is withdrawn.

The invention also provides a method of making a device of the kind described, in which method:

the cover is prepared by cutting a portion of flexible tube from a reel on which the tube is wound, which portion serves to constitute the cover, and by sealing one end of the portion by means of a hot press;

the cover is inserted in the tube by means of a rod, and a few millimeters of the cover is folded back over the tube;

a predetermined quantity of an impedance-matching medium is inserted inside the cover, and then the plug rod is inserted into the cover; and the device prepared in this way and accompanied by a cutting tool is packaged individually.

Advantageously, suction is established outside the cover prior to inserting the impedance-matching medium and the plug rod into the cover, after which the suction is eliminated.

BRIEF DESCRIPTION OF THE DRAWINGS

Other characteristics and advantages of the invention appear from the following description of an embodiment that is given by way of non-limiting example and with reference to the accompanying figures, in which:

FIG. 2 is a longitudinal section view of a device for protecting a cover;

FIG. 2A is a cross-section of the protective tube on IIA—IIA in FIG. 2;

FIG. 3 shows a step during which a vacuum is established by a vacuum pump and the rod is withdrawn from the cover, as explained below;

FIG. 4 shows the probe that is to be used;

MORE DETAILED DESCRIPTION

A protective device 1 is described below. It comprises a tube 2 (FIG. 2) also referred to as a protective element or as a protective tube or as a vacuum chamber. The tube 2 is hollow and open at both ends. On its inside surface it has four ridges 12 constituted by rectilinear projecting portions extending over the entire length of the tube. The four ridges 12 are uniformly distributed over the inside surface of the tube (FIG. 2A). The tube 2 is for single use and it is delivered sterile.

Figures 6, 7:
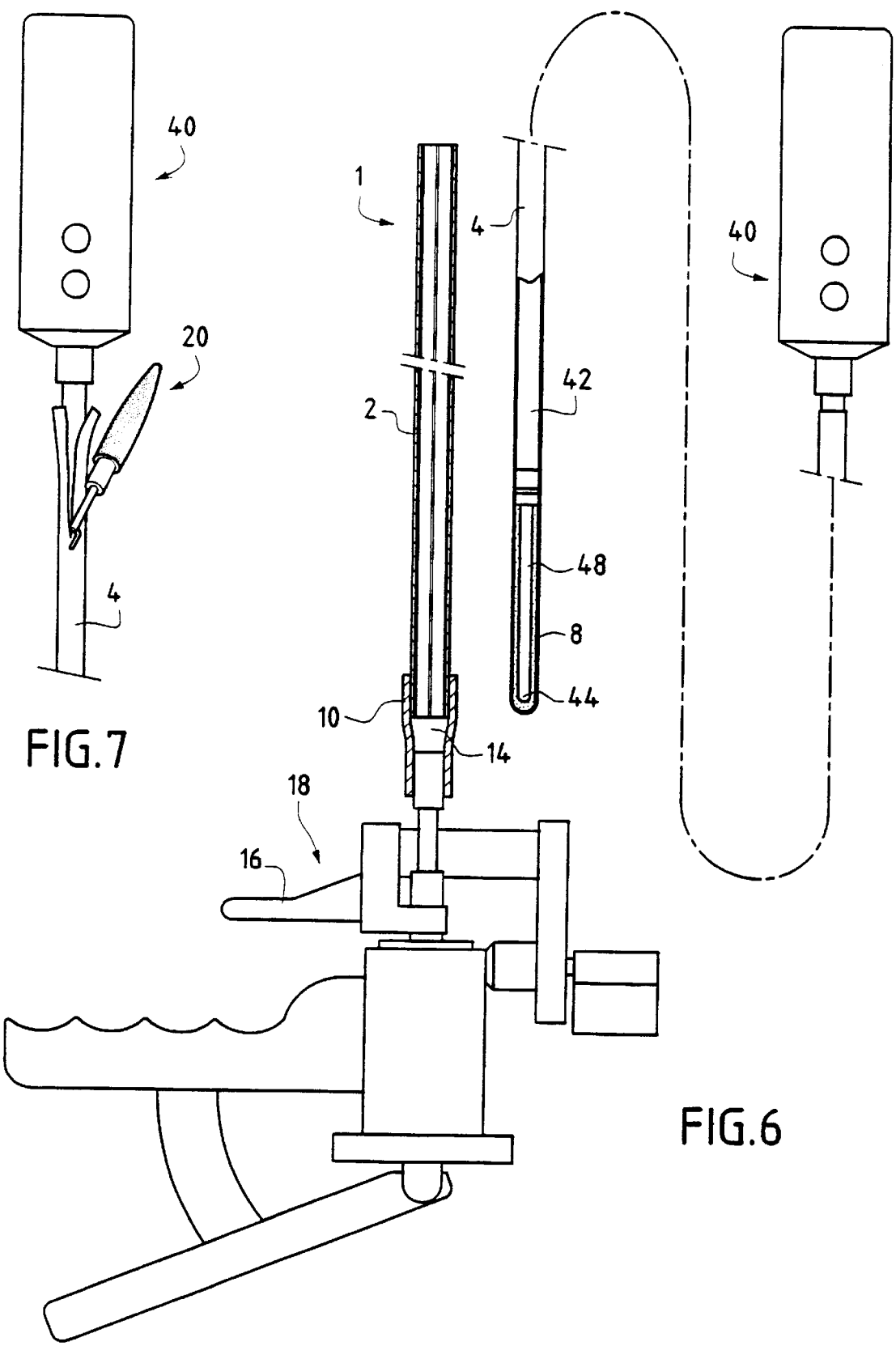
FIG. 6 shows the probe covered by the cover and ready for use.
FIG. 7 shows the step of cutting open the cover after a probe fitted with the cover has been used, for the purpose of removing a used cover so that it can be discarded.

The tube 2 contains a flexible cover 4 that is substantially tubular in shape, being closed at one end and open at the other end. At its closed end, the cover 4 is completely covered by the tube 2. At its open end, the cover 4 is folded back over the outside surface of the tube 2. The ridges 12 are means for enabling localized areas to be created where the cover 4 does not come into contact with the inside wall of the tube 2, thereby enabling suction to propagate, as described below. The diameter of the cover 4 is suitable for enabling it to fit substantially closely against the inside surface of the tube 2. The cover 4 is designed to cover a plunger 42 of a probe 40 (FIG. 6). The probe 40 itself is known and it is not described in detail herein. The probe 40 has a guide endpiece 44 for guiding a cradle 48 carrying transducers suitable for performing measurements. The length of the cover 4 is sufficient to ensure that, in use, only the cover 4 comes into contact with the patient. The cover 4 is delivered sterile and is for single use only. The cover 4 protects the patient from any risk of being contaminated by pathogens carried by the probe 40. The cover 4 is automatically tested individually for leakproofing while it is being put into place.

The cover 4 contains an impedance-matching medium, in particular an acoustic gel 8 (FIG. 2) which is delivered sterile, for single use, biocompatible, non-toxic, and better still edible, so as to avoid any risk in the event of the cover 4 rupturing while it is inside the patient. The acoustic gel 8 is placed in the closed end of the cover 4. The acoustic gel 8 should never come into contact with the patient. Its function is to ensure that ultrasound signals from the probe 40 are transmitted well and with little refraction relative to the tissues.

A plug rod 6 is engaged in the cover 4. The plug rod 6 projects beyond the tube 2. The plug rod 6 is constituted by a long tube which is closed at its end engaged inside the cover 4 and open at its other end. The plug rod 6 serves to keep the acoustic gel 8 at the end of the cover 4. The plug rod 6 also constitutes means for keeping the cover 4 in place substantially in contact with the tube, in particular during transport. The plug rod 6 is never in contact with the patient, it is for single use only, and it is delivered sterile.

A flexible silicone coupling 10, for single use only and delivered sterile, is mounted on the tube 2 adjacent to the closed end of the cover 4. As described below, the coupling 10 constitutes means for facilitating insertion of the envelope 4 inside the tube 2. The coupling 10 never comes into contact with the patient. The coupling 10 is of a shape suitable for establishing a leakproof and flexible connection between the tube 2 and a hand pump 16 (FIG. 3).

The hand pump 16 is a conventional vacuum pump which is not described in detail herein. It has a trigger 18 for establishing suction when in the position shown in FIG. 4 and for releasing suction when in the position shown in FIG. 5. It never comes into contact with the patient nor does it come into contact with the cover 4, so it is not subject to sterility constraints, however it can be decontaminated in a solution of glutaraldehyde, if necessary. The hand pump 16 is not for single use only and it is not sterile.

A cutting tool 20 (FIG. 1) has a handle 22 of plastics material, more precisely of polycarbonate, and a crescent-shape blade 24 made of stainless metal. For safety reasons, it is difficult to gain access to the cutting edge of the blade 24. A cap 26 protects access to the blade 24. The cutting tool 20 is for single use only and it is delivered sterile.

Figure 1:
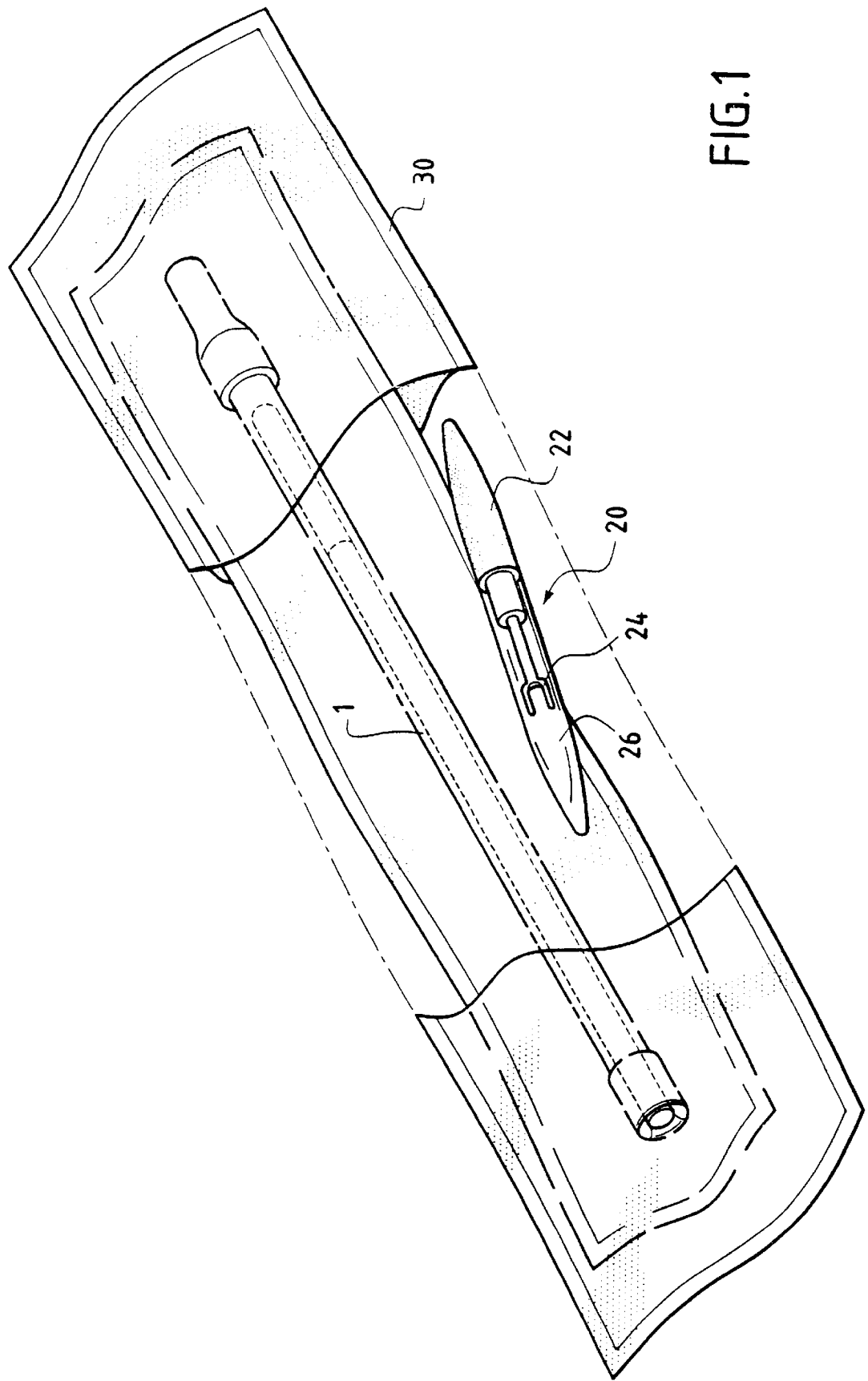
FIG. 1 is a perspective view of a device for protecting a cover in a package, showing how the device is presented to a user of a probe.

The protective device 1 is delivered together with the cutting tool 20 in a transparent package 30, as shown in FIG. 1.

The dimensions and the materials of the device are given below by way of specific example.

The tube 2 is 610 millimeters long, has an inside diameter of 9 millimeters, and an outside diameter of 10 millimeters. The tube 2 is made of polycarbonate.

The cover 4 is 560 millimeters long, has an inside diameter 6.5 millimeters, and an outside diameter of 6.9 millimeters. The cover 4 is made of styrene ethylene buta-diene styrene (SEBS); i.e. it is made of a thermoplastic elastomer.

The plug rod 6 is 610 millimeters long, has an inside diameter of 5.4 millimeters, and an outside diameter of 7 millimeters. The plug rod 6 is made of polyethylene.

The acoustic gel 8 is sterile and edible. The cover 4 contains about one cubic millimeter thereof.

The coupling 10 is 25 millimeters long, has an inside diameter of 6.5 millimeters, and an outside diameter of 12.5 millimeters. The coupling 10 is made of silicone.

The use of the device is described below. The user seeks to fit the cover 4 on the probe 40.

To do this, the user begins by verifying that the package 30 is intact, puts on sterile gloves, and cuts open one end of the package 30. The protective device 1 is taken carefully out of the package 30. The hand pump 16 is connected to the coupling 10. The user holds the protective device 1 in the vertical position taking care to position the acoustic gel 8 at the bottom, and then establishes a vacuum in a closed space 14 defined by the coupling 10, the hand pump 16, the cover 4, and the tube 2. The vacuum is established by actuating the trigger 18 of the hand pump 16. A few strokes of the hand pump should suffice. The cover 4 becomes separate from the plug rod 6. The purpose of the ridges 12 is to facilitate transmission of the vacuum between the cover 4 and the inside of the tube 2. The function of the hand pump is thus to establish a gaseous vacuum inside the space 14 so as to inflate the cover 4, thereby enabling the plug rod 6 to be withdrawn and then the probe 40 to be inserted, as explained below.

The user carefully withdraws the plug rod 6 by hand, so as to avoid entraining the cover 4 or any acoustic-gel 8 in this operation (FIG. 3).

Figure 4:
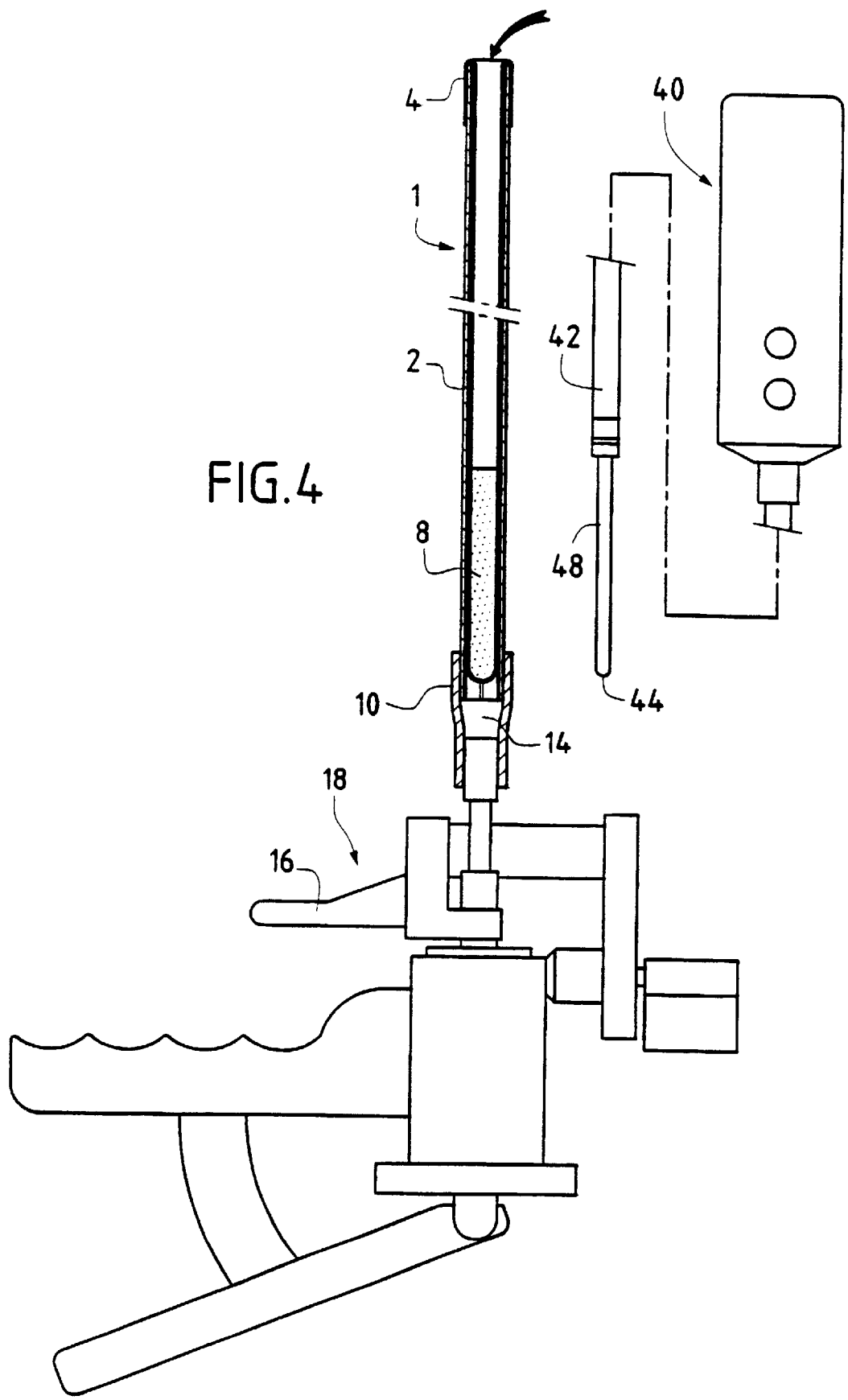
FIG. 4 is a view analogous to the preceding figure but in which the rod has been fully withdrawn, and furthermore

The user then verifies that the vacuum is still present, thus ensuring that the cover 4 is leakproof (FIG. 4).

Figure 5:
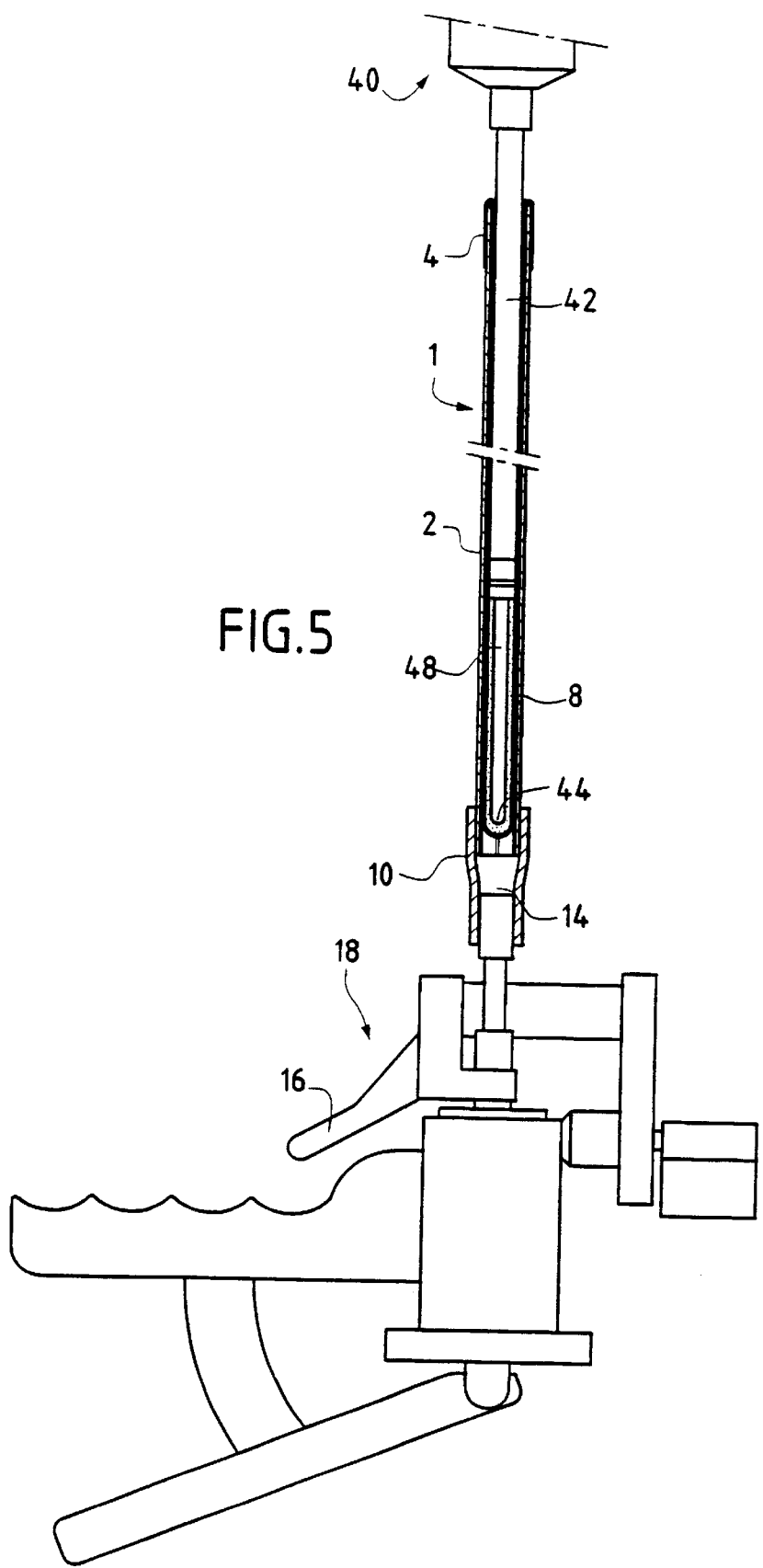
FIG. 5 shows the probe inserted inside the cover.

While keeping the tube 2 vertical, the user then inserts the plunger 42 of the probe 40 until the end of the probe dips into the acoustic gel 8, and then verifies that the guide endpiece 44 has reached the end of the cover 4. At this point the user gently releases the suction by acting on the trigger 18 of the hand pump 16 (FIG. 5). The end of the cover 4 which was initially folded down over the outside surface of the tube 2 is then slid onto the plunger 42 of the probe 40.

Thereafter the probe 40 covered in the cover 4 is withdrawn from the tube 2. The user then checks that there are no bubbles around the transducer cradle 48. The probe 40 covered in this way by the cover 4 is then ready to be inserted in the patient (FIG. 6) and must be handled with the usual precautions required when handling a sterile object. Once the probe 40 has been put into place, the user can take measurements.

Since the time required for fitting the cover is very short, the user does not put the cover 4 into place on the probe 40 until the last moment, immediately prior to use. For insertion via the mouth, it is advantageous to use a spacer between the teeth (not shown) so as to protect the probe 40 from being bitten. In addition, such a spacer can be of assistance in stabilizing the depth to which the probe 40 is introduced, with internal rotation being performed by means of the plunger 42. The acoustic gel 8 also enables the transducer cradle 48 to rotate properly without twisting the cover 4.

While the probe 40 is being withdrawn from the patient, it is preferable to withdraw the cover 4 together with the probe 40 itself. After the probe 40 fitted with the cover has been withdrawn, the user rinses the entire cover abundantly with antiseptic soap, while taking care not to wet the handle of the probe 40.

The user takes the sterile cutting tool 20 from its package and uses the blade 24 of the tool to slit open the cover 4, starting from its open end (FIG. 7). The cover 4 is thus cut along its entire length. The cover 4 is cut lengthwise so as to avoid running any risk of damaging the probe 40.

The user removes the used and cut-open cover from the probe 40 and discards the cover 4. The user disposes of the acoustic gel 8 present on the plunger 42 and rinses the plunger 42 of the probe 40 abundantly in water so as to eliminate all traces of the acoustic gel 8.

The method of making the protective device 1 is described below. To implement this method, the following items are used: a syringe having a capacity of 50 cubic centimeters with a diameter of 2 millimeters and a cannula having a length of 600 millimeters; a polyethylene rod having a diameter of 4 millimeters and a length of 650 millimeters; a hot press; and a vacuum pump; these items are not shown.

Initially the cover 4 is prepared and inserted inside the tube 2.

To do this, a reel is available having 500 meters to 1000 meters of flexible tube wound thereon, which tube is used to make the cover. The tube is cut into portions that are 560 millimeters long. One end of each portion is sealed by means of the hot press. This makes the cover 4.

To make the coupling 10, a rolled-up hose is cut into portions that are each 25 millimeters long. Thereafter, the coupling 10 is inserted on the tube 2.

The polyethylene rod is used to insert the cover 4 inside the tube 2 and the cover 4 is folded back onto the tube 2 over about 4 millimeters.

Thereafter the acoustic gel 8 is inserted inside the cover 4. To do this, the syringe is filled with acoustic gel 8 while ensuring that no bubbles form. Bubbles of air are eliminated via the cannula. The vacuum pump is connected to the coupling 10. Suction is established. Then about 1 cubic millimeter of acoustic gel 8 is inserted in the inflated cover 4. Thereafter the plug rod 6 is inserted above the acoustic gel 8. Suction is eliminated. The device prepared in this way is packaged individually, accompanied by a cutting tool 20. A label is stuck on the package. A parcel of five packages is made up and a second label is placed on the parcel which is ready to be sold.

What is claimed is:

1. A device for protecting an intracorporeal probe, comprising:
    (a) a probe cover, comprising a hollow tube of flexible material configured and dimensioned for application over an intracorporeal probe, wherein the tube is closed at one end and open at its other end; and
    (b) a cover protector, comprising:
        (i) a hollow tubular protective element arranged for application over the probe cover such that at least a portion of the probe cover is inserted into the cover protector, wherein the protective element is open at both ends; and
        (ii) a plurality of means for establishing localized regions of contact between the cover protector and the probe cover, wherein the plurality of means comprise internal ridges disposed substantially parallel to the longitudinal axis of the protective element of the cover protector.

2. The device of claim 1, wherein the cover protector further comprises means for facilitating insertion of the probe cover into the cover protector.

3. The device of claim 2, wherein the means for facilitating insertion comprise a flexible coupling mounted on that one of the open ends of the cover protector that is adjacent to the closed end of the probe cover, so as to enable temporary suction to be established between the probe cover and the cover protector at the closed end of the probe cover.

4. The device of claim 1, wherein the internal ridges are continuous and extend substantially from one end of the protective element to the other, so as to enable temporary suction to be established between the probe cover and the cover protector at the closed end of the probe cover.

5. The device of claim 1, wherein the probe cover is folded back over the cover protector at the end of the cover protector that is remote from the closed end of the probe cover.

6. The device of claim 1, wherein the cover protector further comprises means for holding the probe cover substantially against the inner wall of the protective element of the cover protector.

7. The device of claim 1, wherein the probe cover contains an impedance-matching medium.

8. The device of claim 7, wherein the impedance-matching medium is an acoustic impedance-matching medium.

9. The device of claim 7, wherein the impedance-matching medium is disposed substantially at the closed end of the probe cover.

10. The device of claim 7, wherein the impedance-matching medium is a gel.

11. The device of claim 10, wherein the impedance-matching medium is a biocompatible.

12. The device of claim 11, wherein the impedance-matching medium is edible.

13. The device of claim 1, wherein the cover protector is sterilized.

14. The device of claim 13, wherein the cover protector is packaged in a sterilizable, sealed package that is at least partially transparent.

15. The device of claim 1, further comprising an intracorporeal probe.

16. The device of claim 15, wherein the probe cover is of a length sufficient to cover the outside surface of the intracorporeal probe.

17. The device of claim 15, wherein the intracorporeal probe has an ultrasound measuring element.

18. The device of claim 1, wherein the flexible material of the probe cover is selected from the group consisting of silicone, natural rubber, and synthetic rubber.

* * * * *